(12) United States Patent
Selvin et al.

(10) Patent No.: US 8,110,404 B2
(45) Date of Patent: Feb. 7, 2012

(54) LUMINESCENT LANTHANIDE BINDING CHELATES

(75) Inventors: Paul R. Selvin, Urbana, IL (US);
Pinghua Ge, Champaign, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 434 days.

(21) Appl. No.: 12/092,604

(22) PCT Filed: Nov. 14, 2005

(86) PCT No.: PCT/US2005/041337
§ 371 (c)(1),
(2), (4) Date: May 5, 2008

(87) PCT Pub. No.: WO2007/055700
PCT Pub. Date: May 18, 2007

(65) Prior Publication Data
US 2008/0299675 A1    Dec. 4, 2008

(51) Int. Cl.
*G01N 21/76* (2006.01)
*C07D 245/02* (2006.01)
(52) U.S. Cl. .................................. 436/172; 540/465
(58) Field of Classification Search ............... 436/172; 540/465
See application file for complete search history.

(56) References Cited

U.S. PATENT DOCUMENTS
4,500,356 A * 2/1985 Crump et al. ............... 106/717

OTHER PUBLICATIONS
De Jong et al. CAS Accession No. 1983:470686.*

* cited by examiner

*Primary Examiner* — Joseph Kosack
(74) *Attorney, Agent, or Firm* — Richard Aron Osman

(57) ABSTRACT

Lanthanide chelates derived from diazacrown ethers having two ethyliminodiacetic acid side chains have increased ability to bind lanthanide ions.

21 Claims, No Drawings

LUMINESCENT LANTHANIDE BINDING CHELATES

This work was supported by Federal Grant Nos. NIH AR44420 and NSF 9984841. The U.S. government has rights in any patent issuing on this application.

FIELD OF THE INVENTION

The field of the invention is luminescent lanthanide binding chelates.

BACKGROUND OF THE INVENTION

Luminescence Resonance Energy Transfer (LRET) is a modification and improvement on the widely used technique of fluorescence resonance energy transfer (FRET), and can be widely used in accurately determining the distances between two sites bearing energy donor and energy acceptor respectively in a bio-molecule [1]. In LRET, one of the energy donors is a luminescent lanthanide atom enhanced by a small chelate (1):

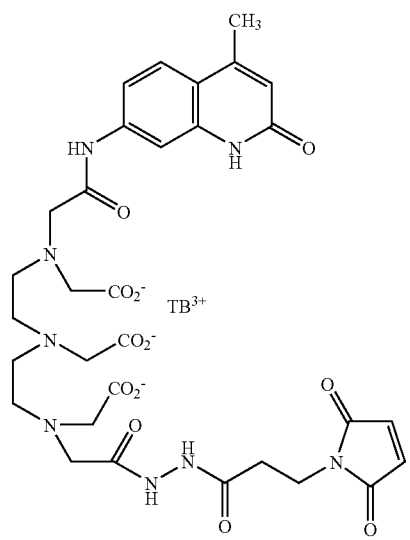

and the acceptor is a conventional (organic) fluorophore.

LRET has great distance accuracy and range; ability to resolve multiple D-A distances; great ability to isolate signal from proteins labeled with both donor and acceptor, even in the presence of proteins labeled only with donor or only with acceptor; and less sensitivity of energy transfer to orientation of dyes (which is often unknown).

The fundamental advantages of LRET arise because the donor emission is long-lived with millisecond lifetime compared to nanosecond lifetime of acceptor or conventional dyes, is sharply-spiked (peaks of a few nanometer width), has a high quantum yield [2], and is unpolarized [3]. Also, the chelate's atomic structure has also been determined [4].

An order of magnitude greater accuracy in distance-determination is achieved with LRET because the energy transfer process is dominated by the distance between the donor and acceptor, and their relative orientations play only a minor role in determining energy transfer efficiency. (A worst case scenario is 12% uncertainty in distance determination due to orientation effect.) This advantage is because terbium donor emission is unpolarized [3]. This contrasts to FRET where the errors due to orientation effects can be unbounded. We have shown that angstrom changes due to protein conformational changes can readily be measured with LRET [5, 6].

A 100-fold improvement in signal to background (S/B) is achieved with LRET. Specifically, energy transfer can be measured with essentially no contaminating background, a stark-contrast to FRET. By temporal and spectral discrimination, donor emission and acceptor emission—both intensity and lifetime—can be independently measured. This leads to dramatically improved signal to background compared to FRET. Specifically, in LRET the acceptor emission due only to energy transfer—called sensitized emission—can be measured with no background. Contaminating background in FRET when trying to measure energy transfer via an increase in acceptor fluorescence, arises from two sources: direct excitation of the acceptor by the excitation light and donor emission at wavelengths where one looks for acceptor emission. In LRET both sources are eliminated. For example, by choosing an acceptor such as fluorescein and looking around 520 nm, donor emission is dark. By using pulsed excitation and collecting light at 520 nm only after a few tens of microseconds, all the direct acceptor emission (which has nanosecond lifetime) has decayed away. Samples that contain donor-only or acceptor-only can be spectrally and temporally discriminated against with LRET. Often when labeling proteins, particularly in living cells, one gets an unknown distribution of donor-donor, donor-acceptor, and acceptor-acceptor mixture. In FRET this makes distance-determination difficult. In LRET, sensitized emission from acceptor arises only from donor-acceptor labeled complex. Energy transfer of this D-A labeled complex can then be determined by comparing the lifetime of sensitized emission ($\tau_{ad}$), which decays with micro- to millisecond lifetime of donor that is transferring energy to the acceptor, with the donor-only lifetime ($\tau_d$): $E=1-\tau_{ad}/\tau_d$. This ability to measure energy transfer even in complex labeling mixtures is essential for the LRET studies on ion channels [5, 13].

We have published a number of papers on LRET (partially reviewed [7, 8]) showing its advantage in model systems such as DNA oligomers [9, 10], the ability to measure distance changes of an angstrom reliably even on large protein complexes such as actomyosin [11, 12], and most recently, in ion channels in living cells [5,13]. Other workers have now successfully used the technique on DNA-protein complexes [14-17], actomyosin [18], protein-protein interactions in cells [19], and detection of binding of many different biomolecules [20-22].

The current chelate-complex (1) works moderately well with both terbium and europium. The disadvantage of such chelate-complexes is that either the relatively low stability constant or fast dissociation and transmetalation kinetics limits their application in physiological environment. The lanthanide complex of 1,4,7,10-tetraazacyclododecane N,N',N'',N'''-tetraacetic acid (DOTA) (2A) has been shown to be an excellent lanthanide chelate with a large thermal and kinetic stability constant, and has been widely used as a contrast agent in MRI imaging. Its non-reactive form of luminescent chelate, (DOTA)-cs124 (2B) has been synthesized.

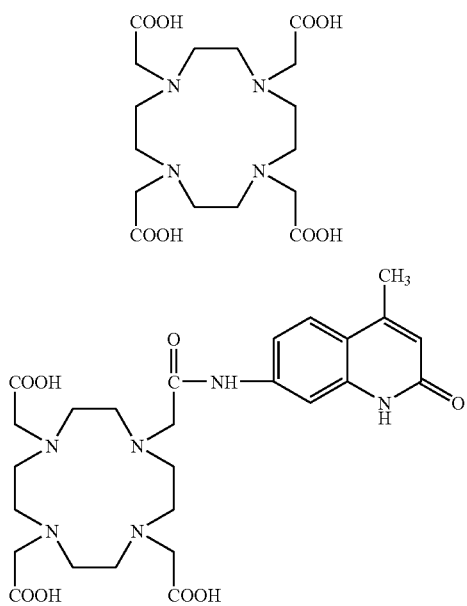

But it has its limitations as well. The binding of DOTA and lanthanide ions is a kinetically slow process [23]. Furthermore, as for luminescent lanthanide probes, amine- or thiol-reactive groups facilitate attachment to a biomolecule. However, neither amine-reactive nor thio-reactive forms of DOTA-based fluorescent chelates have been reported.

The class of macrocycles known as crown ethers has been widely studied since their metal ion-coordinating capabilities were first reported by C. J. Pedersen (*J. Am. Chem. Soc.* 1967, 89, 7017). Derivations of the crown ether include the replacement of one or more of the ring's oxygen atoms with nitrogen atoms resulting in azacrown ethers and/or the attachment of one or more side chains to the ring to form a so-called lariat or armed crown ether. There are numerous publications on the metal-complexing properties of diazacrown ethers containing side chains attached to the nitrogen atoms of the macrocycle (see e.g. Chi et al, *Bull. Korean Chem. Soc.* (2002) 23(5) 688-692; Gonzalez-Lorenzo et al, *Inorg Chem.* (2005) 44(12): 4254-4262; Wang et al., *Chinese Chemical Letters*, (2003) 14(6): 579-580; Peters et al, *J. Chem. Soc., Dalton Trans.*, (2000) 4664-4668; and I. A. Fallis, *Annu. Rep. Prog. Chem. A* 94 (1998) 351-387).

We have synthesized a new type of lanthanide chelate derived from diazacrown ethers. Our chelates contain two ethyliminodiacetic acid side chains and have increased ability to bind lanthanide ions.

SUMMARY OF THE INVENTION

One aspect of the invention is a crown ether lanthanide chelate of Formula I:

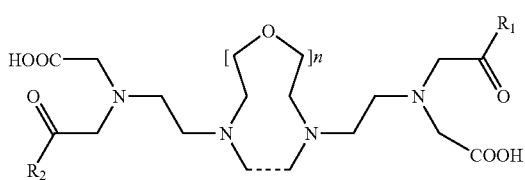

or a dianhydride thereof wherein: the dotted line (----) represents a single bond or [$CH_2$—O—$CH_2$]n'; $R_1$ and $R_2$ are independently selected from OH, a photosensitizer, a linker optionally conjugated to a biomolecule, and a biomolecule; and n and n' are independent integers; wherein one or more oxygen and/or carbon atoms of the central ring of Formula I may be optionally replaced by a protected nitrogen atom.

In a particular embodiment of the lanthanide chelate of Formula I, n is 1 and the dotted line represents a single bond. In further embodiments, n is 1, the dotted line represents a single bond, $R_1$ is OH, and $R_2$ is OH.

In another embodiment of the lanthanide chelate of Formula I, n is 1 and the dotted line represents $CH_2$—O—$CH_2$. In further embodiments, n is 1, the dotted line represents $CH_2$—O—$CH_2$, $R_1$ is OH, and $R_2$ is OH.

In one embodiment of the lanthanide chelate of Formula I, $R_1$ is a photosensitizer selected from the group consisting of an aminoquinolone, an aminocoumarin, an aminoacetophenone, an aminobenzophenone, an aminofluorenone, an aminoxantone, an amino-azaxanthone, an aminoanthraquinone, and an aminoacridone sensitizer. In specific embodiments, the photosensitizer is selected from the group consisting of carbostyril 124 (7-amino-4-methyl-2-quinolinol), coumarin 120 (7-amino-4-methyl-2-coumarin), and coumarin 124 (7-amino-4-(trifluoromethyl)-2-coumarin).

In one embodiment of the lanthanide chelate of Formula I, $R_2$ is a linker for conjugation to a biomolecule. In particular embodiments, the linker is a thiol-reactive or amine-reactive linker. In specific embodiments, the linker is selected from the group consisting of a maleimide moiety, a bromoacetamide moiety, a pyridyldithio moiety, an iodoacetamide moiety, a methanethiosulfonate moiety, an isothiocyanate moiety, and an N-hydroxysuccinimide ester moiety.

In further embodiments of the lanthanide chelate of Formula I, $R_1$ is a photosensitizer and $R_2$ is a biomolecule or a linker optionally conjugated to a biomolecule.

In one embodiment, the lanthanide chelate of Formula I is complexed with a lanthanide ion selected from the group consisting of $Tb^{3+}$, $Eu^{3+}$, $Lu^{3+}$, $Dy^{3+}$, and $Gd^{3+}$.

Another aspect of the invention is a method for determining an interaction between biomolecules based on fluorescence resonance energy transfer, the method comprising: conjugating a lanthanide chelate of Formula I via a linker at the $R_2$ position to a first biomolecule, wherein $R_1$ is a photosensitizer; labeling a second biomolecule with a fluorescent energy acceptor; and measuring the resulting fluorescence.

DETAILED DESCRIPTION OF SPECIFIC EMBODIMENTS OF THE INVENTION

We disclose a new type of crown ether lanthanide chelate derived from polyaza crown ethers that has increased ability to bind lanthanide ions. In a preferred embodiment, the lanthanide has the following Formula (I):

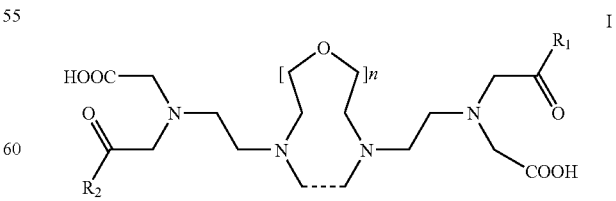

or is a dianhydride thereof (e.g. see structure 13). In Formula I the dotted line (----) represents a single bond or [$CH_2$—O—$CH_2$]n'; $R_1$ and $R_2$ are independently selected from OH, a photosensitizer, a linker optionally conjugated to a biomolecule, and a biomolecule; and n and n' are independent (i.e. the same or different) integers. While the central, crown ether ring of Formula I can be of any size, lanthanide binding capacity decreases with increased ring size. Thus, in preferred embodiments, n and n' are each independently integers from 1 to 10, preferably from 1 to 5, and more preferably from 1 to 3. Equivalent crown ether ring structures may have one or more oxygen or carbon atoms in the ring replaced by a nitrogen atom, resulting in a triaza, tetraaza, etc. crown ethers, provided that the additional nitrogen atoms are protected (e.g. with a methyl, ethyl, or other protecting group) such that only two of the nitrogen atoms of the ring carry the dicarboxylic acid side chains.

Exemplary configurations of the central ring of Formula I include 1-oxa-4,7-diazacyclononane; 1,7-dioxa-4,10-diazacyclododecane; 1,7-diaza-4,10,13-trioxacyclopentadecane; 1,7-diaza 4,10,13,16-tetraoxacyclooctadecane; 1,10-diaza 4,7,13,16-tetraoxacyclooctadecane, etc. In one embodiment of the lanthanide chelate of Formula I, n is 1 and the dotted line represents a single bond (i.e. the ring is 1-oxa-4,7-diazacyclononane). In further embodiments, n is 1, the dotted line represents a single bond, $R_1$ is OH, and $R_2$ is OH. In another embodiment of the lanthanide chelate of Formula I, n is 1 and the dotted line represents $CH_2$—O—$CH_2$ (i.e. the ring is 1,7-dioxa, 4,10-diazacyclododecane). In further embodiments, n is 1, the dotted line represents $CH_2$—O—$CH_2$, $R_1$ is OH, and $R_2$ is OH. Synthesis of the 1-oxa-4,7-diazacyclononane- and 1,7-dioxa, 4,10-diazacyclododecane-based lanthanide chelates of the invention is detailed in Example 1.

In particular embodiments of the lanthanide chelate, $R_1$ and/or $R_2$ is a photosensitizer. Suitable photosensitizers are known in the art (see e.g. U.S. Pat. Nos. 5,639,615 and 6,740,756) and include, for example, aminoquinolones, aminocoumarins, aminoacetophenones, aminobenzophenones, aminofluorenones, aminoxantones, amino-azaxanthones, aminoanthraquinones, and aminoacridones. In particular embodiments of the lanthanide chelate, $R_1$ is a photosensitizer selected from the group consisting of carbostyril 124 (7-amino-4-methyl-2-quinolinol), coumarin 120 (7-amino-4-methyl-2-coumarin), and coumarin 124 (7-amino-4-(trifluoromethyl)-2-coumarin). Synthesis of lanthanide chelates having a carbostyril 124 photosensitizer is detailed in Example 1.

In particular embodiments of the lanthanide chelate, $R_1$ and/or $R_2$ is a linker for conjugation to a biomolecule. In preferred embodiments the linker is thiol-reactive (see e.g. Ge P, Selvin P R, Bioconjug Chem. (2003) 14:870-876; Chen J, Selvin P R, Bioconjug Chem. (1999) 10:311-315) or amine-reactive (see Li M, Selvin P R, Bioconjug Chem. (1997) 8:127-132). Exemplary linkers for conjugation to a biomolecule include a maleimide moiety, a bromoacetamide moiety, a pyridyldithio moiety, an iodoacetamide moiety, a methanethiosulfonate moiety, an isothiocyanate moiety, and an N-hydroxysuccinimide (NHS) ester moiety. Synthesis of a lanthanide chelate having a maleimide linker is detailed in Example 1 (see structure 17). An exemplary lanthanide chelate having an NHS ester linker is depicted below (3).

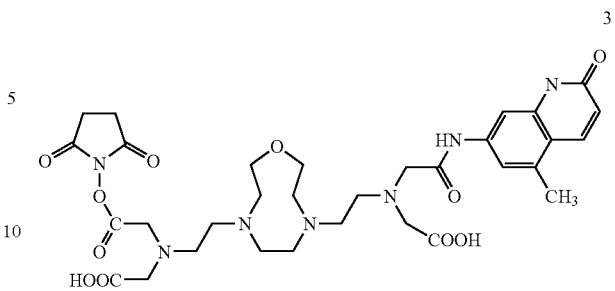

3

In particular embodiments of the lanthanide chelate, $R_1$ and/or $R_2$ is a biomolecule optionally conjugated to the lanthanide chelate via a linker. Examples of biomolecules include proteins, polynucleotides, peptides, living cells, etc. In one embodiment, $R_1$ and $R_2$ are polylysine molecules, suitable for use in MRI applications. The chelate may be directly conjugated to the biomolecule, for example as when using anhydride-based conjugation with an amine- or thiol-containing biomolecule such as an amine-modified DNA (e.g. DNA having a 5'C6-amino linker; see Li M, Selvin P R, Bioconjug Chem. (1997) 8:127-132).

In particular embodiments the lanthanide chelate is complexed with a lanthanide ion. In particular embodiments, the lanthanide ion is selected from $Tb^{3+}$, $Eu^{3+}$, $Lu^{3+}$, $Dy^{3+}$, and $Gd^{3+}$.

The disclosed lanthanide chelates are useful in the same applications as prior lanthanide chelates (e.g. Gd-DTPA), such as FRET, LRET, MRI, etc, or as phasing agents in solving the crystal structures of biomolecules. One aspect of the invention is a method for determining an interaction between biomolecules based on fluorescence resonance energy transfer (FRET). The method comprises conjugating a lanthanide chelate of Formula I via a linker at the $R_2$ position to a first biomolecule, wherein $R_1$ is a photosensitizer; labeling a second biomolecule with a fluorescent energy acceptor; and measuring the resulting fluorescence. The fluorescent energy acceptor can be any conventional fluorophore used in FRET assays such as tetramethylrhodamine iodoacetamide (TMRIA), fluorescein iodoacetanide (FIA), ATTO 465 maleimide, etc. The first and second biomolecules may be any molecule pair analyzable in FRET-based assays, for example as in FRET-based detection of antibody/antigen binding, enzyme/substrate reactions, receptor/ligand binding, etc. Resulting fluorescence is measured using routine methodology (see Example 2).

Example 1

Synthesis and Characterization of Luminescent Lanthanide Binding Chelates

We synthesized a new type of lanthanide chelate derived from N,N'-disubstituted 12- or 9-membered (poly)-oxa-polyaza macrocycles (4,5).

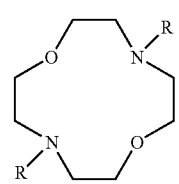

4

-continued

5

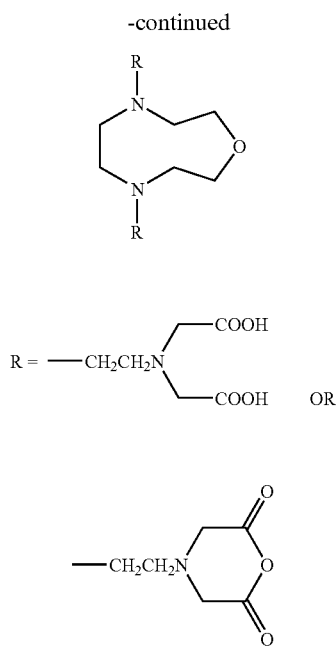

6

R = —CH₂CH₂N(COOH)(COOH)  OR

7

—CH₂CH₂N(with cyclic anhydride)

Structurally, these new compounds are similar to that of DTPA (8), with the key features include that they are 10- or 9-dentate chelates with four ionizable carboxylate groups.

8

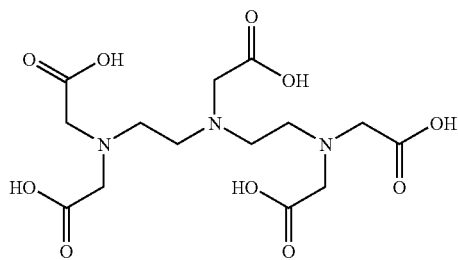

Yet, a significant difference of these chelates is that they have macrocycle units incubated in the backbone, which can increase their binding ability to lanthanide ions. Because lanthanide ions can take up to 10 coordination atoms, the new chelates provide better protection to the lanthanide ions from solvent molecule attacks, and thus longer lifetime in aqueous media compared to that of DTPA chelate (3), which is an 8-dentate chelate. For instance, TTHA (9) is a 10-dentate linear chelate. The $Tb^{3+}$ lifetime of its TTHA-cs124 complex is longer than that of DTPA-cs124 (2.10 ms vs 1.55 ms) [24]. And also because the structures of these chelates are more open and flexible compared to that of DOTA chelates, the binding of lanthanide ions to the chelates is quicker than that of DOTA and lanthanide ions. In addition to forming a stronger binding luminescent lanthanide probes, these chelates can also serve as good MRI contrast agents by binding with $Gd^{3+}$ [25].

Like DTPA, the free carboxylic acid form of the chelate can be easily converted to dianhydride form (7). The dianhydride form allows attachment of an antenna molecule and either an amine-reactive group or a thiol-reactive group to the chelate to make a luminescent probe for LRET or FRET experiments.

The syntheses of the chelates are straightforward. 1,7-dioxa-4,10-diazacyclododecane (9) or 1,4,7-octahydro-oxadiazonine (14) (both commercially available) are reacted with N,N-bis[(tert-butoxycarbonyl)methyl]-2-bromoethylamine (10) [26], followed by hydrolysis under either acidic or basic conditions to form the free acid form of chelate (12). The free acid form of chelates can then be converted to dianhydride form (13) by reaction with acetic anhydride ($Ac_2O$):

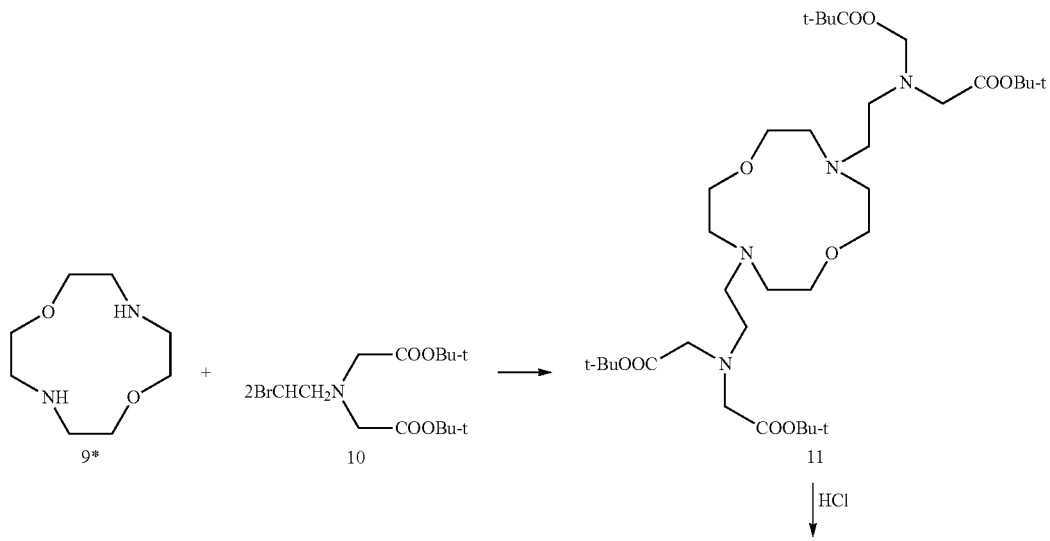

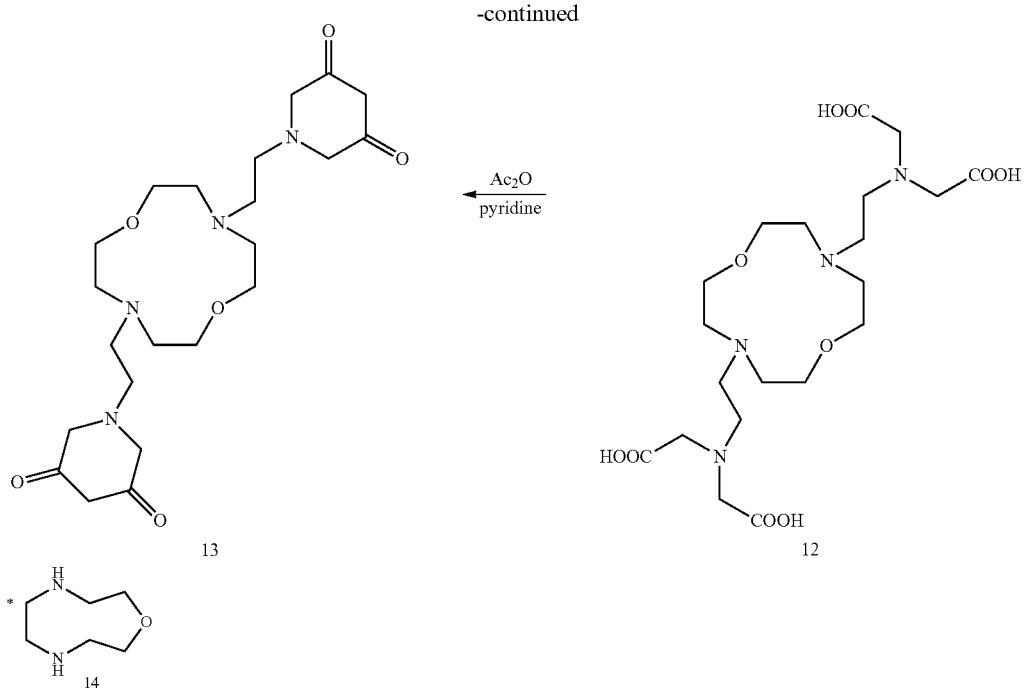

To synthesize amine or thiol-reactive lanthanide chelates, similar methods used for synthesizing DTPA based chelates are employed. The formed dianhydride form of chelate is consequently reacted with an antenna molecule (e.g. cs124) and a bi-functional thiol-reactive or amine-reactive compound in a one-pot reaction to form corresponding luminescent chelates. For example, to synthesize a thiol-reactive luminescent probe, the dianhydride form of chelate (13) can react with cs124 first in a ~1:0.7 molar ratio, followed by reaction with β-maleimidopropionic acid hydrazide (EMPH) (16) to form a thio-reactive maleimide form of luminescent lanthanide probe (17):

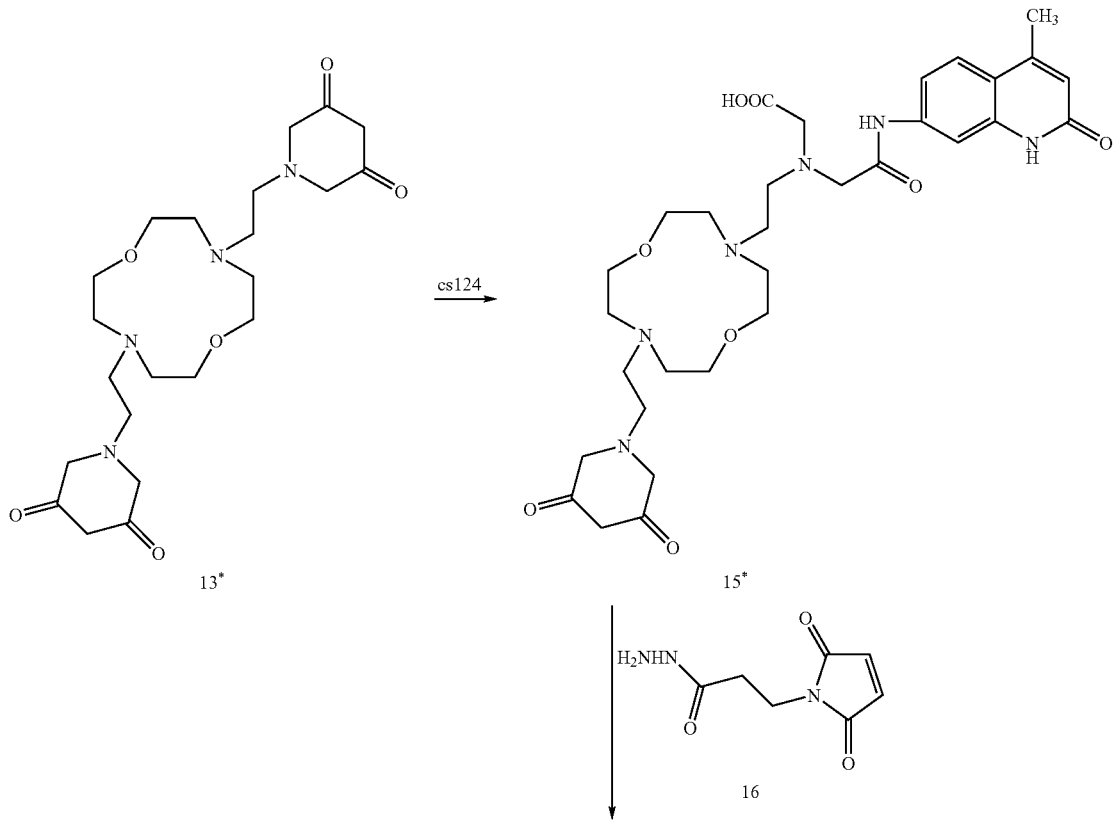

-continued
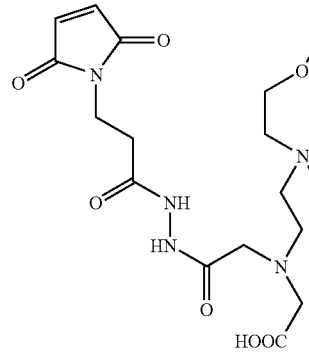
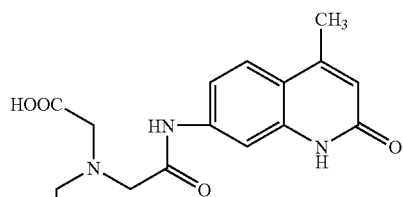
17*
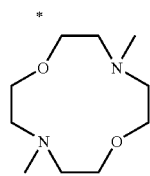 can be replaced by 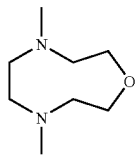

We have synthesized the free acid form of 1-oxa-4,7-diazacyclononane and 1,7-dioxa-4,10-diazacyclododecane based luminescent lanthanide chelates (4, 5). This free acid form of chelates was attached to cs124 by reacting with isobutyl chloroformate first, followed by reacting with cs124 (18, 19).

The 1-oxa-4,7-diazacyclononane based, thio-reactive forms of chelates (20, 21) were also synthesized.

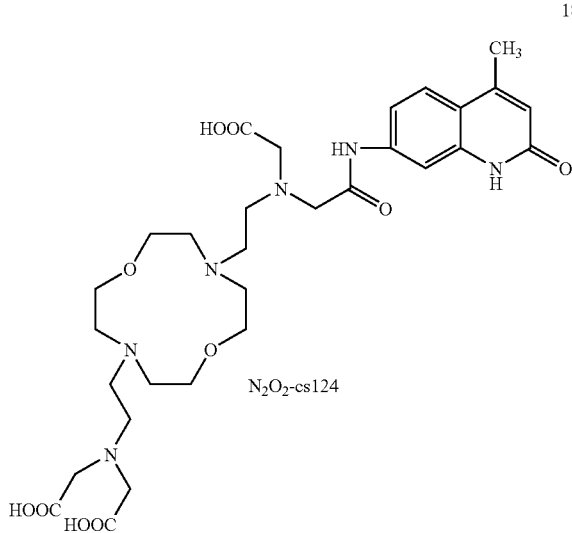

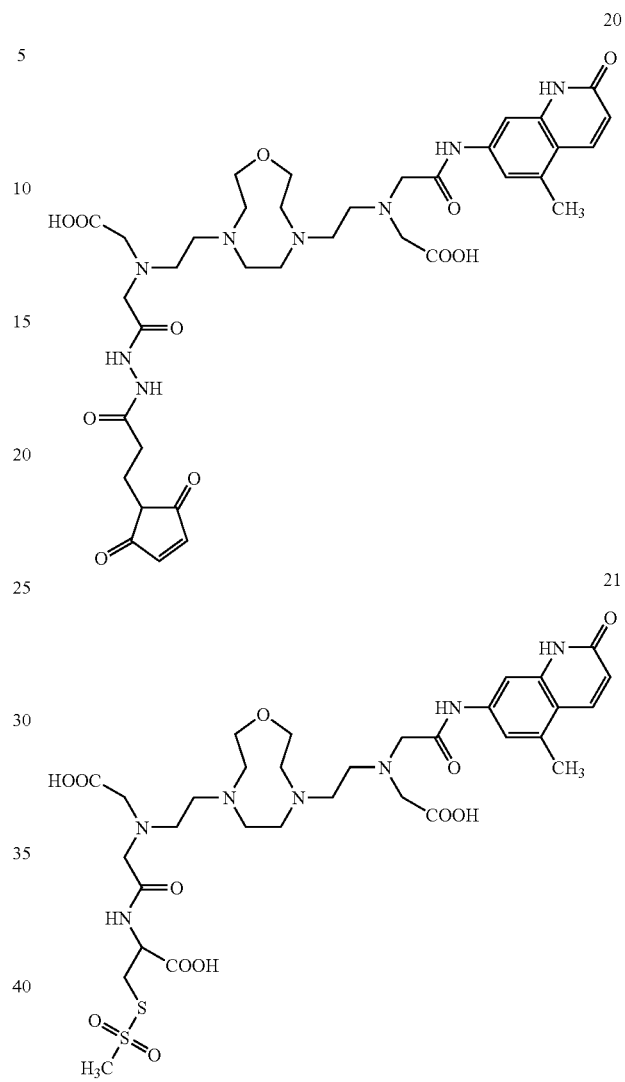

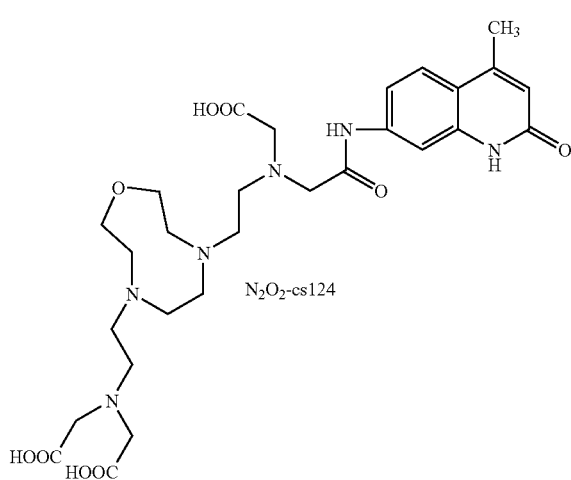

All of these chelates were characterized by mass spectroscopy and UV-vis absorption spectroscopy. Luminescent spectroscopy results are listed in Table 1. Comparing the number of water molecules coordinated to lanthanide ions in the non-reactive form of chelates, we can clearly see the new chelates provide better protection to lanthanide ions from solvent molecule attack. In the case of $Tb^{3+}$—$N_2O$-cs124, there is practically no solvent molecule (0.02 on average) coordinated to the metal ion. Generally, the 1-oxa-4,7-diazacyclononane derived chelates exhibit better photophysical properties in terms of brightness, lifetimes and no of water coordinated.

TABLE 1

Photophysics Data of Luminescent Lanthanide Binding Chelates

| Metal | Chelates | $\tau H_2O$ | $\tau D_2O$ | $\tau H_2O/\tau D_2$ | No of waters | Relative Brightness |
|---|---|---|---|---|---|---|
| $Tb^{3+}$ | DTPA-cs124 | 1.55 | 2.63 | 0.59 | 1.1(24) | 1 |
| | $N_2O$-cs124 | 1.89 | 1.91 | 0.99 | 0.02 | 1.3 |
| | $N_2O_2$-cs124 | 2.50 | 2.88 | 0.87 | 0.22 | 0.2 |

TABLE 1-continued

Photophysics Data of Luminescent Lanthanide Binding Chelates

| Metal | Chelates | $\tau H_2O$ | $\tau D_2O$ | $\tau H_2O/\tau D_2$ | No of waters | Relative Brightness |
|---|---|---|---|---|---|---|
| | $N_2O_2$-cs124-EMPH | 1.93(81%)<br>0.72(19%) | | | | 0.4 |
| $Eu^{3+}$ | DTPA-cs124 | 0.62 | 2.42 | 0.26 | 1.26(24) | 1 |
| | $N_2O$-cs124 | 1.0 | 2.5 | 0.4 | 0.63 | 0.7 |
| | $N_2O_2$-cs124 | | | | | N/A |
| | $N_2O_2$-cs124-EMPH | 1.03(41%)<br>0.60(22%)<br>0.04(37%) | | | | 0.3 |

Example 2

LRET Measurements in Myosin

This experiment, which is adapted from Burmeister Getz et al. (Biophys J. (1998) 74:2451-2458), demonstrates that LRET measurements on purified heavy meromyosin (HMM) are capable of measuring the requisite distances between catalytic and light chain domains, that the measured distance in the absence of nucleotide is consistent with the crystal structure, and that myosin adopts a different conformation upon binding actin and actin plus ADP.

Acceptor labeling: A 5:1 mole ratio of 5-tetramethyl-rhodamine iodoacetamide (TMRIA) (Molecular Probes, Eugene, Oreg.) to purified heavy meromyosin (HMM) (isolated from rabbit skeletal muscle) is reacted overnight on ice in rigor buffer (1 mM EGTA, 5 mM $MgCl_2$, 20 mM MOPS, pH 7.0). HMM concentrations during labeling are approx. 15 µM. The reaction is quenched by the addition of 10 mM dithiothreitol (DTT), and passed over a G-75 Sephadex size-exclusion column to remove free TMRIA. The goal is to achieve 2 TMRIA/HMM, with one TMRIA at each Cys707 site on the HMM dimer.

Donor labeling: Donor chelate is placed on the light chain domain as follows. A thio-reactive maleimide form of luminescent lanthanide chelate (17) is prepared as described in Example 1. A solution of $TbCl_3$ is added at a 0.9:1 molar ratio to chelate at pH 7 at millimolar concentration, and the metal is allowed to bind for 30 min on ice. An approx. 20-fold excess of the metal-containing chelate is then added to chicken gizzard regulatory light chain (RLC) in exchange buffer with 5 mM tris-(2-carboxyethyl)phosphine hydrochloride (TCEP). The reaction is allowed to proceed for more than an hour (often overnight) at pH 7.0 on ice and quenched with 10 mM DTT. Gizzard RLC contains a unique cysteine (Cys108, equivalent in position to Val103 on the skeletal RLC, based on sequence alignment (Collins, *J. Muscle Res. Cell Motil.* (1991) 12:3-25).

Exchange reaction: Endogenous RLC is replaced with chelate-labeled gizzard RLC as follows. A 5- to 10-fold excess of Tb-gizzard RLC is added to HMM (either unlabeled or TMRIA-labeled) in exchange buffer (1 mM ADP, 50 mM KCl, 10 mM EDTA, 10 mM KH2PO4 (or 50 mM 3-(N-morpholino)propanesulfonic acid, MOPS), pH 7.0), and the solution is heated to 34° C. for 15 min, followed by cooling on ice and the addition of TES (pH 7.0) and then $MgCl_2$ to final concentrations of 100 mM and 15 mM (5 mM free Mg), respectively. Unincorporated RLC is eliminated, and the solvent changed, by passing over a G-75 column equilibrated in rigor buffer. Incorporation of gizzard RLC into skeletal HMM is confirmed by SDS-PAGE.

To check for nonspecific binding of the gizzard RLC to HMM, the two are mixed at concentrations identical to those used for exchange (5-8 µM HMM, 25-80 µM gizzard RLC). This mixture is left on ice for 15 min instead of being heated to 34° C., and then passed over a G75 column. During the heating step of the exchange reaction, 1 mM ADP is used to preserve the enzymatic activity of the HMM. In the presence of 1 mM ADP, both the $K^+$-ATPase and actin-activated $Mg^{2+}$-ATPase activities of HMM are unchanged after gizzard RLC exchange relative to untreated HMM.

Lanthanide luminescence measurements: All terbium emission data is recorded on a laboratory-built spectrophotometer described previously [9] and upgraded to include a CCD for spectral measurements [4]. Samples are placed in a quartz cuvette (either 3 mm×3 mm or 2 mm×2 mm inner dimensions) at room temperature. The concentration of HMM is typically 1 µM in rigor buffer. The concentration of actin, when present, is typically 4-10 µM. This actin concentration ensures complete binding of HMM. The terbium donor is excited with 400-1600 excitation pulses from a nitrogen laser (337 nm, 5-ns pulsewidth, 40-Hz repetition rate), and terbium emission (546 nm) is acquired after passing through a grating spectrometer with a photon-counting photomultiplier attached to a multichannel analyzer (2-ms resolution).

Curve-fitting and energy transfer analysis: Multiexponential fits are made with Tablecurve (Jandel Scientific, Marin, Calif.). Donor-only data are fit to two exponentials and show no residual structure. Donor-acceptor data are fit to three exponentials and also show no residual structure. The efficiency of energy transfer is calculated from the lifetimes of donor luminescence as $1-(\tau_{D/A}/t_D)$, where $\tau_D$ and $\tau_{D/A}$ are the donor excited state lifetimes in the absence and presence of acceptor, respectively. For each experiment, donor-only and donor-acceptor samples are prepared simultaneously, and all energy transfer calculations pair the donor-acceptor measurement with the corresponding donor-only control. This pairwise method of comparison yields highly reproducible results and is superior to determining energy transfer by comparing the average of donor-only lifetimes to the average of donor-acceptor lifetimes. A paired sample t-test is used to determine the statistical significance of differences in energy transfer measurements between experimental conditions (HMM alone, HMM+actin, HMM+actin+ATP, HMM+actin+ADP).

Polarization measurements: Steady-state anisotropy measurements $[(I_{||}-I_{\perp})\Box(I_{||}+2\ I_{\perp})]$ of TMRIA bound to myosin are performed according to standard methods using 514-nm vertically polarized excitation, a rotatable analyzer, and a second analyzer placed at 45° to eliminate detection polarization effects. In addition, an aperture is placed in the emission path to limit the numerical aperture, and a CCD is used as the detector [7]. Blank measurements on unlabeled myosin and unlabeled myosin bound to actin are subtracted from all signals. Measurements are performed at room temperature at ~0.5 µM TMRIA in a 3 mm×3 mm cuvette.

Steady-state anisotropy measurements on the terbium-labeled gizzard RLC exchanged into HMM (without TMRIA) are performed similarly, except that excitation is with vertically polarized 337-nm pulsed light, and the emission is passed through a single analyzer and a chopper before being detected by the CCD. The polarization sensitivity of the optics is determined by assuming that the anisotropy of a Tb-DTPA-cs124 chelate freely diffusing in solution is zero. (The spectrometer has a bias in favor of horizontally polarized light.)

Results: The results show that LRET measurements on HMM are capable of measuring the requisite distances between catalytic and light chain domains, that the measured distance in the absence of nucleotide is consistent with the crystal structure, and that myosin adopts a different conformation upon binding actin and actin plus ADP.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

REFERENCES (1) Selvin, P. R. *Annual Review of Biophysics and Biomolecular Structure* 31, 275-302 (2002).
(2) Xiao, M.; Selvin, P. R. *J. Am. Chem. Soc.* 123, 7067-7073 (2001).
(3) Reifenberger, J. G. et al, *Biophysics. J.* 82, 430a (2002).
(4) Selvin, P. R. et al. *Inorg. Chem.* 35, 700-705 (1996).
(5) Cha, A., et al. *Nature,* 402, 809-813 (1999).
(6) Xiao, M., et al. *Proc. Nat'l. Acad. Sci., USA,* 95, 15309-15314 (1998)
(7) Selvin, P. R. *IEEE J of Selected Topics In Quantum Electronics: Lasers in Biology* 2, 1077-1087 (1996).
(8) Selvin, P. R. in Applied Fluorescence in Chemistry, Biology and Medicine (eds. Rettig, W.; Strebmenl, B.; Schrader, S.& Seifert, H.) 457-487 (Springer Verlag, New York, 1999).
(9) Selvin, P. R.; Hearst, J. E. *Proc. Natl. Acad. Sci, USA* 91, 10024-10028 (1994).
(10) Selvin, P. R.; Hearst, J. E. U.S. Pat. No. 5,622,821 (1994).
(11) Xiao, M., et al. *Proc. Nat'l. Acad. Sci., USA,* 95, 15309-15314 (1998).
(12) Xiao, M., et al. *Nat. Struct. Biol,* 10, 402-8 (2003).
(13) Posson, D. et al. *Nature.* 436(7052):848-51 (2005).
(14) Heyduk et al. *J. Biol. Chem.* 272, 19763-19770 (1997).
(15) Heyduk et al. *Anal. Biochem.* 248, 216-227 (1997).
(16) Callaci, S. et al. *Mol. Cell.* 3, 229-238 (1999).
(17) Heyduk. E.; Heyduk, T. *J. Biol. Chem.* 274, 3315-3322 (1999).
(18) Xu, J.; Root, D. D. *J. Struct. Biol.* 123, 150-161 (1998).
(19) Root, D. D. *Proc. Natl. Acad. Sci., USA* 94, 5685-5690 (1997).
(20) Mathis, G. *Clinical Chem.* 39, 1953-1959 (1993).
(21) Mathis, G. *Clinical Chem.* 41, 1391-1397 (1995).
(22) Vazquez-Ibar, J. L. et al. *Proc. Natl. Acad. Sci. USA* 99, 3487-3492 (2002).
(23) Desreux, J. F. *Inorg. Chem.* 19, 1319-1324 (1980).
(24) Li, M. & Selvin, P. R. *J. Am. Chem. Soc.,* 117, 8132-8138 (1995).
(25) Caravan, P.; et al *Chem. Rev.* 99, 2293-2352 (1999).
(26) Williams, M. A. & Rapoport, H. *J. Org. Chem.* 58, 1151-1158 (1993).

What is claimed is:

1. A crown ether lanthanide chelate of Formula I:

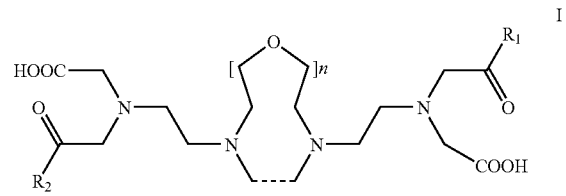

or a dianhydride thereof wherein:
the dotted line (----) represents a single bond or [CH$_2$—O—CH$_2$]n';
R$_1$ is a photosensitizer; and
R$_2$ is selected from OH, a linker optionally conjugated to a biomolecule, and a biomolecule;
n and n' are independent integers from 1 to 3;
wherein one or more oxygen atoms of the central ring of Formula I may be optionally replaced by a protected nitrogen atom such that only the two nitrogen atoms depicted in the central ring of Formula I carry dicarboxylic acid side chains.

2. The lanthanide chelate of claim 1 wherein n is 1 and the dotted line represents a single bond.
3. The lanthanide chelate of claim 1 wherein n is 1, the dotted line represents a single bond, and R$_2$ is OH.
4. The lanthanide chelate of claim 1 wherein n is 1 and the dotted line represents CH$_2$—O—CH$_2$.
5. The lanthanide chelate of claim 1 wherein n is 1, the dotted line represents CH$_2$—O—CH$_2$, and R$_2$ is OH.
6. The lanthanide chelate of claim 1 wherein R$_1$ is a photosensitizer selected from the group consisting of an aminoquinolone, an aminocoumarin, an aminoacetophenone, an aminobenzophenone, an aminofluorenone, an aminoxantone, an amino-azaxanthone, an aminoanthraquinone, and an aminoacridone sensitizer.
7. The lanthanide chelate of claim 1 wherein R$_1$ is a photosensitizer selected from the group consisting of carbostyril 124 (7-amino-4-methyl-2-quinolinol), coumarin 120 (7-amino-4-methyl-2-coumarin), and coumarin 124 (7-amino-4-(trifluoromethyl)-2-coumarin).
8. The lanthanide chelate of claim 1 wherein R$_2$ is a linker for conjugation to a biomolecule.
9. The lanthanide chelate of claim 1 wherein R$_2$ is a thiol-reactive linker for conjugation to a biomolecule.
10. The lanthanide chelate of claim 1 wherein R$_2$ is an amine-reactive linker for conjugation to a biomolecule.
11. The lanthanide chelate of claim 1 wherein R$_2$ is a linker for conjugation to a biomolecule, wherein the linker is selected from the group consisting of a maleimide moiety, a bromoacetamide moiety, a pyridyldithio moiety, an iodocetamide moiety, a methanethiosulfonate moiety, an isothiocyanate moiety, and an N-hydroxysuccinimide ester moiety.
12. The lanthanide chelate of claim 1 wherein R$_2$ is a linker conjugated to a biomolecule.
13. The lanthanide chelate of claim 1 wherein R$_2$ is a biomolecule.
14. The lanthanide chelate of claim 1 that is complexed with a lanthanide ion.
15. The lanthanide chelate of claim 1 that is complexed with a lanthanide ion selected from the group consisting of Tb$^{3+}$, Eu$^{3+}$, Lu$^{3+}$, Dy$^{3+}$, and Gd$^{3+}$.

16. A method for determining an interaction between biomolecules based on fluorescence resonance energy transfer, the method comprising:
   conjugating a lanthanide chelate of claim 14 via a linker at the $R_2$ position to a first biomolecule;
   labeling a second biomolecule with a fluorescent energy acceptor; and
   measuring fluorescence resonance energy transfer between the chelate and the acceptor to determine an interaction between the biomolecules.

17. The lanthanide chelate of claim 1 wherein none of the oxygen atoms of the central ring of Formula I is replaced by a protected nitrogen atom.

18. The lanthanide chelate of claim 1 wherein the central ring of Formula I is selected from the group consisting of: 1-oxa-4,7-diazacyclononane; 1,7-dioxa-4,10-diazacyclododecane; 1,7-diaza-4,10,13-trioxacyclopentadecane; 1,7-diaza-4,10,13,16-tetraoxacyclooctadecane; and 1,10-diaza-4,7,13,16-tetraoxacyclooctadecane.

19. The lanthanide chelate of claim 1 wherein the central ring of Formula I is selected from the group consisting of: 1-oxa-4,7-diazacyclononane; 1,7-dioxa-4,10-diazacyclododecane; 1,7-diaza-4,10,13-trioxacyclopentadecane; 1,7-diaza-4,10,13,16-tetraoxacyclooctadecane; and 1,10-diaza-4,7,13,16-tetraoxacyclooctadecane, and wherein none of the oxygen atoms of the central ring is replaced by a protected nitrogen atom.

20. The lanthanide chelate of claim 1 wherein the central ring of Formula I is selected from the group consisting of: 1-oxa-4,7-diazacyclononane; 1,7-dioxa-4,10-diazacyclododecane; 1,7-diaza-4,10,13-trioxacyclopentadecane; 1,7-diaza-4,10,13,16tetraoxacyclooctadecane; and 1,10-diaza-4,7,13,16-tetraoxacyclooctadecane, and wherein none of the oxygen atoms of the central ring is replaced by a protected nitrogen atom, and wherein $R_1$ is a photosensitizer selected from the group consisting of an aminoquinolone, an aminocoumarin, an aminoacetophenone, an aminobenzophenone, an aminofluorenone, an aminoxantone, an amino-azaxanthone, an aminoanthraquinone, an aminoacridone sensitizer, carbostyril 124 (7-amino-4-methyl-2-quinolinol), coumarin 120 (7-amino-4-methyl-2-coumarin), and coumarin 124 (7-amino-4-(trifluoromethyl)-2-coumarin).

21. The lanthanide chelate of claim 1 having a structure selected from the group consisting of:

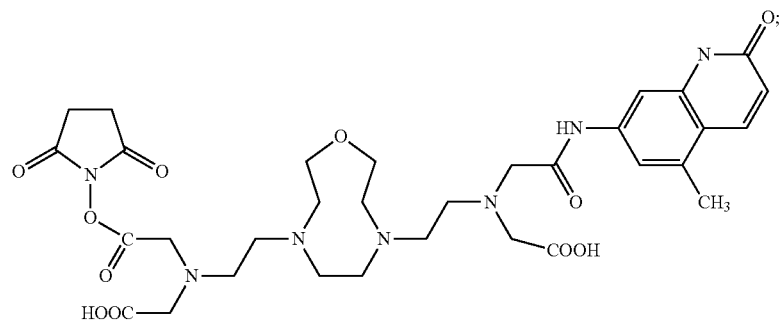

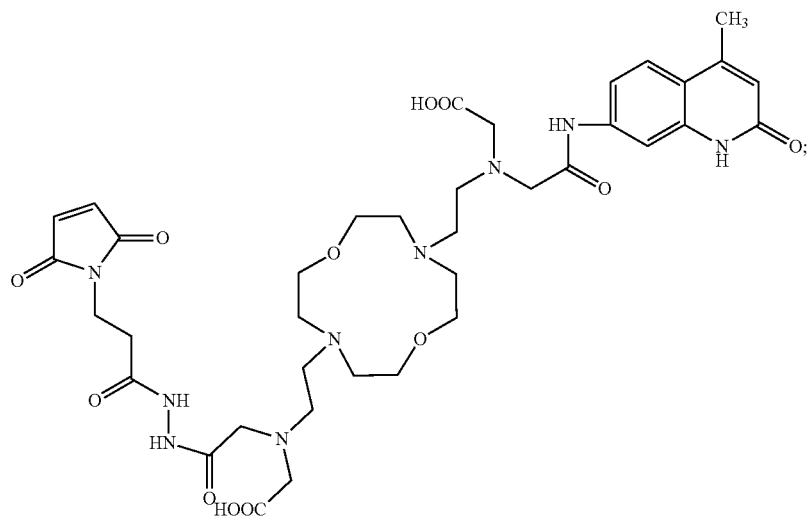

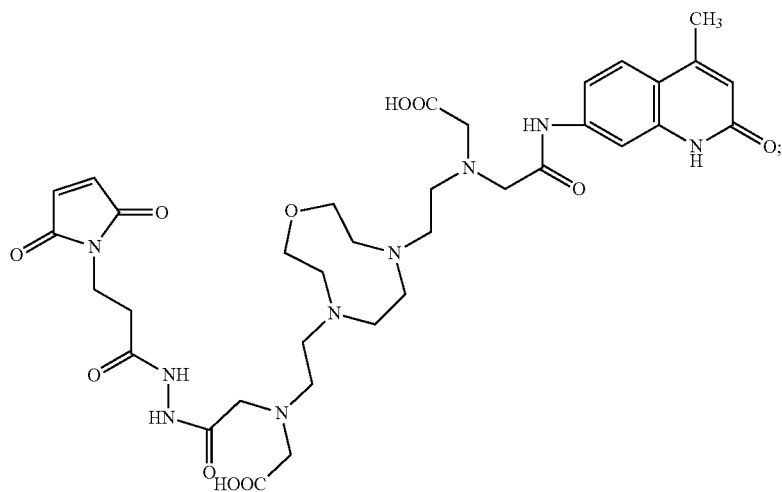
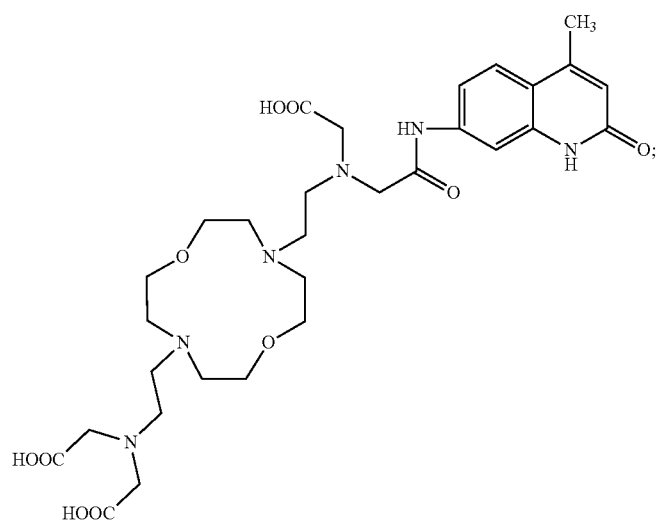
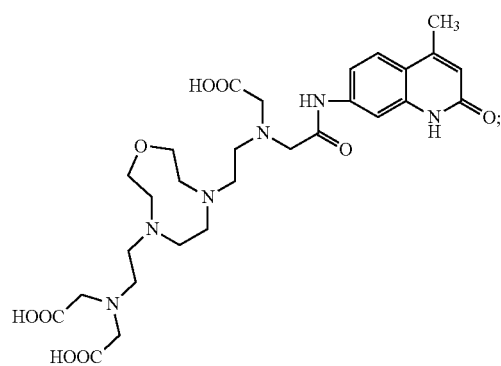

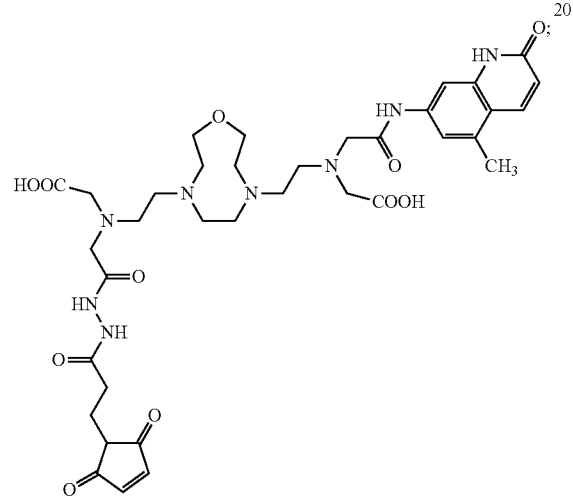
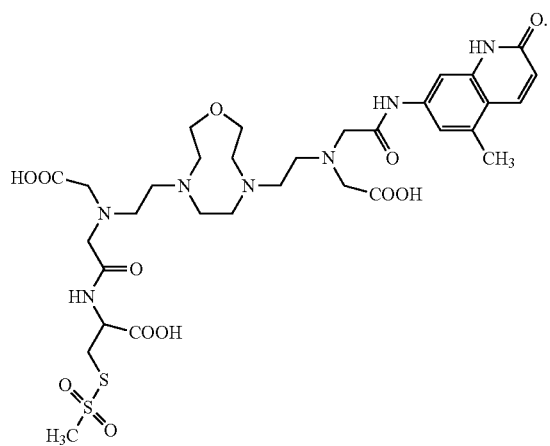
* * * * *